United States Patent [19]

Bourgeois et al.

[11] Patent Number: 4,931,577

[45] Date of Patent: Jun. 5, 1990

[54] NOVEL ORGANIC MERCURIAL DERIVATIVES WITH ANTISEPTIC CHARACTER

[75] Inventors: Michel Bourgeois, Lyon; Roger Chatelin; Daniel Wattiez, both of Lozanne, all of France

[73] Assignee: Institut Textile de France, Bagneux Cedex, France

[21] Appl. No.: 254,734

[22] Filed: Oct. 7, 1988

[30] Foreign Application Priority Data

Oct. 8, 1987 [FR] France ............................. 87 14157

[51] Int. Cl.$^5$ ..................... C07F 3/12; C08F 216/14
[52] U.S. Cl. ................... 556/123; 556/121; 556/122; 556/128; 556/126; 556/334; 556/240
[58] Field of Search ............. 556/121, 128, 122, 123, 556/126; 526/334, 240

[56] References Cited

U.S. PATENT DOCUMENTS 3,332,924  7/1967  Van de Castle et al. ............ 526/334
3,676,408  7/1972  Schultz et al. ...................... 526/334
4,556,721  12/1985  Wattiez et al. ..................... 556/128

FOREIGN PATENT DOCUMENTS 0116489  8/1984  European Pat. Off. .
2119066  8/1972  France .

Primary Examiner—Joseph L. Schofer
Assistant Examiner—T. McDonald
Attorney, Agent, or Firm—Shenier & O'Connor

[57] ABSTRACT

The novel antiseptic mercurial derivatives according to the invention have at least one benzene ring and comprise: a) at least one radical HgX in which X is selected from F,Cl,Br, I, OH, $CH_3$ COO, CN, SCN, $NO_3$, OB-$(OH)_2$, b) and, bonded to a benzene ring, at least one group—OR or—COOR in which R is a functional group capable of intervening in a reaction of polymerization or of polyaddition. The preferred derivative is 2-chloromercuri 4-tertiobutyl phenol allyl-ether. They may intervene in grafting reactions for the protection of a polymeric support, or in reactions of copolymerization.

5 Claims, No Drawings

NOVEL ORGANIC MERCURIAL DERIVATIVES WITH ANTISEPTIC CHARACTER

FIELD OF THE INVENTION

The present invention relates to novel organic mercurial derivatives which present antiseptic characteristics.

BACKGROUND OF THE INVENTION

A large number of currently used derivatives of this type are known, including mercurobutol, mercurophene, mercurosal, mercurochrome.

U.S. Pat. No. 4,556,721 in particular has already disclosed derivatives of mercurobutol used for the protection of supports, especially textile supports. These derivatives comprised a functional group bonded to the phenol ring of the mercurobutol, said group being capable of intervening in a reaction of polymerization or of polyaddition; they presented the bioactive properties of the mercurobutol. Among the functional groups, the allyl, vinyl or acrylic groups were mentioned.

However, it has been observed that the presence of the phenol ring presented limits in the operation of the reaction of polymerization. The phenol function has an inhibiting action which limits the development of the reaction, and which reduces the yield thereof. In this way, despite the interest that the derivatives of mercurobutol described in the above-mentioned patent present, their use on an industrial scale is limited by this characteristic peculiar to the phenol function.

Organic mercurial derivatives have now been found, and this is the subject matter of the present invention, which have antiseptic characteristics and which do not present the limitation observed.

SUMMARY OF THE INVENTION

The organic mercurial derivatives according to the invention comprise, in known manner, at least one benzene ring. Moreover, they comprise at least one radical HgX, in which X is selected from F, Cl, Br, I, OH, CH$_3$COO, CN, SCN, NO$_3$, OB(OH)$_2$, and, bonded to a benzene ring, a group —OR or —COOR, in which R is a functional group capable of intervening in a reaction of polymerization or of polyaddition. In particular, R is an allyl, vinyl or acrylic group.

Thus, when it it question of the group —OR, the pehnol function is blocked by the functional group and no longer has any inhibiting action during the reaction of polymerization or of polyaddition. The derivatives present the antiseptic characteristics even after they have been employed in a reaction of polymerization or of polyaddition.

The radical HgX is itself preferably bonded to a benzene ring.

The derivative preferably comprises, bonded to a benzene ring, at least one alkyl group having a number of carbon atoms less than or equal to 5.

The derivative according to the invention has for example the following general formula:

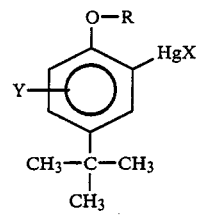

in which Y is either H or HgX.

In particular, it is 2-chloromercuri 4-tertiobutyl phenol allyl-ether.

It is another object of the invention to apply the use of the derivatives of the invention to the protection of a support on which at least one of said derivatives has been fixed by grafting. The support, for example a polymeric textile material, permanently presents the antiseptic characteristics of the derivative which is fixed on its polymeric structure.

It is another object of the invention to protect copolymers obtained by polymerization of a monomer and a mercurial derivative mentioned above. In particular, the acrylic copolymer will be retained, obtained from acrylic acid and by polymerization of this monomer with 2-chloromercuri 4-tertiobutyl phenol allyl-ether. The acrylic copolymer thus obtained may be employed in all the conventional uses of acrylic polymers. It gives the resultant product antiseptic properties.

DETAILED DESCRIPTION OF THE INVENTION

The invention will be more readily understood on reading the following description of the preferred derivative of the invention and of different examples of applications.

The preferred mercurial derivative of the invention is 2-chloromercuri 4-tertiobutyl phenol allyl-ether, of the following formula:

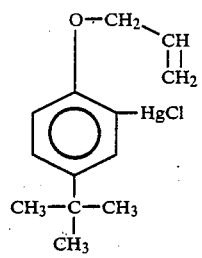

R being, in this particular case, the allyl group.

In order to obtain this derivative, mecurobutol is taken which is a standard product on which allyl bromide is reacted in accordance with the following diagram:

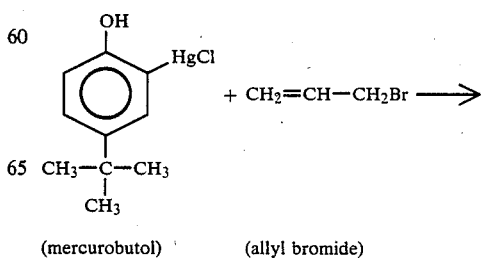

(mercurobutol)    (allyl bromide)

-continued

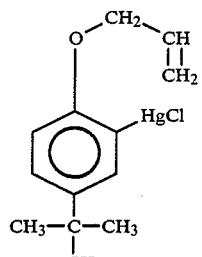

(2-chloromercuri 4-tertiobutyl phenol allyl-ether)

More precisely, 9.3 g of mercurobutol are taken which are dissolved in 50 ml of hot denatured alcohol, in the presence of NaCl. 2 g of potash are carefully added. A thick white precipitate is formed. 4.4 ml of allyl bromide are added in 21 ml of denatured alcohol and the product is mixed with the precipitate which becomes more fluid. The product is heated for two hours at the boiling temperature of the alcohol, then filtered hot. 9.43 g of 2-chloromercuri 4-tertiobutyl phenol allyl-ether are obtained, with a yield of 92%. This product is pure, as may be checked by thin layer chromatography. Its melting temperature is 110° C. It is in the form of a white, water-insoluble powder.

The 2-chloromercuri 4-tertiobutyl phenol allyl-ether is capable of intervening in a reaction of polymerization of the radical type, by opening of its double bond.

In a first application of antiseptic protection of a cotton fabric, said tissue has been grafted with a mixture of acrylic acid and of the derivative of mercurobutol, under the following conditions. A sample of bleached cotton, weighing 6.5 g, is placed in an atmosphere of ozone for 45 minutes at ambient temperature. The fabric is immersed in a test tube containing 200 ml of an aqueous solution containing 10% acrylic acid and 0.01% of 2-chloromercuri 4-tertiobutyl phenol allyl-ether. Degassing is effected with nitrogen in order to drive out the excess ozone, then heated to 100° C. for 1 hour with stirring. The product is then washed with water and extracted with methanol for 1 hour.

The grafted fabric obtained has a graft rate of 2.5%. The mercury rate is obtained by colorimetry at 505 nm with the aid of dithizone, after mineralization of the sample. The mercury rate is 0.15 mg/g of dry fabric.

In order to check the antiseptic protection brought by the grafting employing the derivative of mercurobutol according to the invention, the Swiss standard SN 195-924 has been used, which consists in bringing into contact for a determined time, the fabric and a bacterial suspension of *Staphylococcus Aureus* and in assessing the number of surviving micro-organisms after this contact time (*Staphylococcus Aureus* referency 7625 IP, 25923 ATCC).

The grafted cotton fabric is cut into squares whose sides measure 1.5 cm, three squares being placed in three sterile tubes. In each tube, 0.2 ml of bacterial suspension is poured, in a nutrient medium (at $10^6$ per ml) of *Staphylococcus Aureus*. The drop is deposited on the fabric and not on the walls of the tube. In the first tube, 10 ml of nutrient liquid are poured; it is placed in an oven at 35.5° C. for 24 hours and the cloudiness of the nutrient liquid is observed: the liquid is very cloudy, it has the same cloudiness as that obtained with a non-grafted control sample.

The second and third tubes, after having closed them in sterile manner, are placed in the oven at 35.5° C. for 4 and 7 days respectively. Then 10 ml of nutrient liquid are poured in, the tubes are replaced in the oven for 24 hours, and the cloudiness of the nutrient liquid is observed. In both cases, the nutrient liquid is perfectly clear. Comparatively, the nutrient liquid with the non-treated control sample is very cloudy.

The following observations may be made from these experiments: in the first tube, the fabric grafted with 2-chloromercuri 4-tertiobutyl phenol allyl-ether has not had the time to perform its antiseptic role.

In the other two tubes, after 4 and 7 days of contact, the fabric has inhibited bacterial growth. The non-grafted cotton has no antiseptic property.

In a second application of antiseptic protection of a fabric of polyvinyl chloride fibers, said fabric has been grafted with a mixture of acrylic acid and the derivative of mercurobutol under the following conditions. The tests were carried out in stoppered Pyrex tubes, shaken in a regulated oven. The samples are de-oiled by washing in an alkaline medium. After drying, the samples are treated in ozone for 1 hour at 25° C., then immersed in the test tubes containing the grafting solution (15% acrylic acid; from 0.015 to 0.050% 2-chloromercuri 4-tertiobutyl phenol allyl-ether). Grafting is effected at the temperature of 80°–90° C. for one hour (bath ratio: 1/20). The graft rate and the mercury rate are measured after washing in fresh water and drying: graft rate 5 to 10%; mercury rate from 1.5 to 4 mg/g with respect to the dry weight of the fabric.

The samples thus grafted underwent 5 washing cycles of 30 minutes at 50° C., with a concentration of 2.4 g of washing liquor per liter of softened water. The bath ratio was 1/40. The bath was renewed at each cycle. No reduction in the graft rate nor in the mercury rate was observed.

Microbiological tests in a Petri dish were made on three polyvinyl chloride fabrics. The first, non-grafted, which serves as control, the second, grafted with the aid of the derivative of the invention as stated hereinabove, the third, grafted after 5 washings at 50° C. for 30 minutes (2.4 g/l of washing liquor). The strain employed is *Escherichia Coli* (references 7624 IP, 25922 ATC). The gelose medium is composed, in g/l of distilled water at pH 7.4, of 300 g of beef infusion, 17.5 g of Biocase, 1.5 g of starch, 17 g of gelose.

The gelose is deposited in a standard Petri dish measuring 90×15 mm in a uniform thickness of 4 mm.

The gelose thus deposited is seeded with the aid of a suspension of germs ($10^6$ germs/ml; volume of suspension used=0.5 ml). A square of fabric carefully extracted with methanol is deposited in sterile manner. Each germ deposited on the gelose develops to produce, during stoving at 35.5° C., a circular colony of whitish colour.

After stoving, the preparation is observed under a binocular magnifier. On the periphery of the fabric, the colonies have developed normally. Beneath the fabric, the results differ depending on the three fabrics:

the control fabric, non-grafted but washed with washing liquor in order to eliminate the major part of the micro-organisms present, does not present any antimicrobial activity (normal development beneath the fabric and absence of zone of inhibition around the fabric), the grafted fabric extracted with methanol presents a very clear antimicrobial activity: total absence of colonies beneath the fabric, with a very weak zone of inhibition on the periphery of the fabric (0.1 to 0.5 mm), the grafted fabrics, extracted with methanol then washed 5 times, present the same antimicrobial properties as the second fabric.

From the tests described hereinabove, the following interpretation may be made of the results obtained.

The presence of colonies outside the fabric means that the antiseptic does not diffuse in the gelose. Beneath the fabric and in a zone of 0.1 to 0.5 mm (so-called zone of inhibition) around the fabric, there is no development of colonies. This would mean that the bacteria are inhibited by contact with the active principles present on the fabrics.

Fixation by grafting of the mercurial derivative on a support is not limited to the use of acrylic acid. Two other examples of grafting of a piece of bleached cotton are given hereinafter.

A first piece of bleached cotton is exposed to radiation at 2 Mrad by electronic bombardment then immersed in a solution of 28.5 g of morpholinoethyl methacrylate, 375 ml of alcohol, 350 mg of 2-chloromercuri 4-tertiobutyl phenol allyl-ether and 40 ml of water. After 15 mins. of stirring cold, the piece is washed and extracted with alcohol. The gain in weight is 5.3%, the mercury rate 0.20 mg/g.

A second piece of bleached cotton is exposed to radiation at 2 Mrad by electronic bombardment then immersed in a solution of 25 g of dimethyl-amino ethyl methacrylate, 350 mg of 2-chloromercuri 4-tertiobutyl phenol allyl-ether and 100 ml of water. After 15 mins. stirring cold, the piece is washed and extracted with alcohol. The gain in weight is 4%, the mercury rate 0.17 mg/g.

The mercurial derivatives according to the invention may, thanks to the group R, intervene as reagents in polymerizations or polyadditions. They may therefore be copolymer synthesis agents having antiseptic properties.

An acrylic copolymer has thus been prepared by polymerization of acrylic acid and 2-chloromercuri 4-tertiobutyl phenol allyl-ether. Polymerization is effected in a 1 l reactor equipped with a rising cooler, a 210W bladed stirrer and an oil water-bath. 900 mg of 2-chloromercuri 4-tertiobutyl phenol allyl-ether dissolved in 10 ml of acetic acid are firstly introduced. Then, in the mixture heated to 110° C., a solution of 90% acrylic acid (49.5 ml) (freshly distilled) with 750 mg of benzoyl peroxide and 30 ml of acetic acid, is slowly added. The addition lasts 70 minutes. During this addition, 10 ml of acetic acid are added into the reactor.

After the addition, the mixture is heated for a further 10 minutes with energetic stirring. Then, after cooling, the copolymer is placed in a 1 liter flask equipped with a ground glass stopper and the acetic acid, non-polymerized acrylic acid and water are evaporated in vacuo. Distilled water is added in the flask in order to obtain a liquid copolymer with a total mass of 365.1 g including 45 g of dry matter; this corresponds to 0.12% of mercury in the liquid copolymer.

A polyamide fabric is impregnated in homogeneous manner with the copolymer obtained. After drying, weighing and dosing of the antiseptic (1.1 mg of mercury/g of polyamide), pieces of fabric are cut out which are immersed in tubes of bacterial suspensions of *Escherichia Coli:* 7624 IP, 25922 ATCC in meat-liver-glucose nutrient liquid.

The tubes are shaken in an oven at 35.5° C. An aliquot part of the suspension is removed as soon as the pieces of fabric are immersed (time=0), then after 24 hours' shaking (time=24 hrs). The bacteria are counted on the samples.

TABLE I

| Test No. | Weight of fabric (mg) | Quantity of mercury (μg/ml) | Bacterial concentration (no. of bacteria/ml) | | |
|---|---|---|---|---|---|
| | | | t = O | t = 24 hrs with fabric | t = 24 hrs. without fabric |
| 1 | 162 | 17.8 | 50 | 0 | 5 to 6.10$^8$ |
| 2 | 195 | 21.4 | 300 | 0 | too concentrated |
| 3 | 134 | 14.7 | 1.080 | 0 | too concentrated |
| 4 | 129 | 14.2 | 9.700 | 0 | too concentrated |
| 5 | 149 | 16.4 | 10$^5$ | 0 | too concentrated |
| 6 | 135 | 14.8 | 10$^6$ | 0 | too concentrated |

Table I hereinabove gives, for 6 different tests, the concentrations of the bacterial suspension, at time zero and after 24 hours' shaking, in the presence of fabric impregnated with the copolymer according to the invention and without fabric. Whatever the initial concentration of the bacterial suspension, the antiseptic activity of the copolymer is sufficient for there to be no more bacteria in the solution after 24 hours' shaking.

The invention is not limited to the example which has just been amply described. In particular, the technical product, comprising mercurobutol, may sometimes be a mixture of mercurobutol and of dimercurobutol of formula:

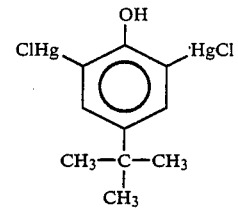

In that case, the preparation described hereinabove and employing allyl bromide leads to obtaining a mixture of two derivatives of the invention, the first comprising one sole radical HgCl bonded to the benzene ring and the second two radicals HgCl bonded to the benzene ring. This mixture made by grafting gives the grafted fabric an antiseptic protection of the same type as that given by 2-chloromercuri 4-tertiobutyl phenol allyl-ether alone.

Furthermore, it is possible easily to obtain other derivatives of the invention, from known antiseptic mercurial products, other than mercurobutol, for example mercurophene, mercurosal, mercurochrome. All these products comprise in their formula at least one benzene ring, at least one radical HgX, in which x is OH and, bonded to the benzene ring, at least one group O—R' or COOR'. Thus, for example, it suffices to react an allyl halide on the mercurial product retained in order to obtain the derivative of the invention in which the group —OR will be the group —O—CH$_2$—CH=CH$_2$.

The derivatives obtained conserve, even after polymerization or polyaddition of the group R, antiseptic properties of the mercurial derivatives from which they were obtained.

What is claimed is:

1. An antiseptic mercurial derivative, which does not comprise any hydroxy group attached to a benzene ring, comprising:
   (a) at least one benzene ring having no hydroxy group attached thereto,
   (b) at least one radical HgX in which X is selected from F, Cl, Br, I, OH, $CH_3COO$, CN, SCH, $NO_3$, $OB(OH)_2$,
   (c) and, bonded to the benzene ring, at least one group —OR or —COOR in which R is a functional group capable of polymerization or polyaddition.

2. The derivative of claim 1, wherein R is an allyl, vinyl or acrylic group, and particularly the allyl group.

3. The derivative of claim 1, wherein the radical HgX is bonded to the benzene ring.

4. The derivative of claim 1, wherein it comprises, bonded to the benzene ring, at least one alkyl group having a number of carbon atoms less than or equal to 5.

5. The derivative of claim 4, characterized by the following general formula:

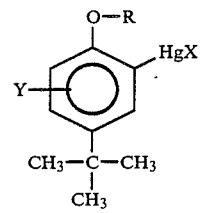

in which Y is H or HgX.